United States Patent
Nakamura et al.

(10) Patent No.: US 7,317,117 B2
(45) Date of Patent: Jan. 8, 2008

(54) SILOXANYL-CONTAINING MONOMERS

(75) Inventors: Masataka Nakamura, Otsu (JP); Mitsuru Yokota, Otsu (JP)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 444 days.

(21) Appl. No.: 10/491,510

(22) PCT Filed: Oct. 2, 2001

(86) PCT No.: PCT/JP01/08680

§ 371 (c)(1),
(2), (4) Date: Apr. 1, 2004

(87) PCT Pub. No.: WO03/042222

PCT Pub. Date: May 22, 2003

(65) Prior Publication Data

US 2004/0249180 A1   Dec. 9, 2004

(51) Int. Cl.
*C07F 7/04* (2006.01)
(52) U.S. Cl. .................................. 556/443
(58) Field of Classification Search ............ 556/443
See application file for complete search history.

(56) References Cited

U.S. PATENT DOCUMENTS 4,709,066 A   11/1987   Chapman

FOREIGN PATENT DOCUMENTS

EP   1354898   10/2003

OTHER PUBLICATIONS

"Polydimethylsiloxanes with vinyl ether end-groups. I. Synthesis and properties as polymerizable wetting agents", European Polymer Journal (1995), 31(6), 521-5, Cazaux et al.*
"Polydimethylsiloxanes with vinyl ether end-groups. I. Synthesis and properties as polymerizable wetting agents", European Polymer Journal (1995), 31(6), 527-532, Cazaux et al.*
European Search Report, dated Aug. 8, 2006, for European Appln. No. EP 01 97 2655.

\* cited by examiner

*Primary Examiner*—Samuel Barts

(57) ABSTRACT

Monomers for polymers having high oxygen permeability, high water content and a low modulus of elasticity are provided, and polymers and ophthalmic lenses comprised of said monomers are provided. They are monomers represented by formula (1) or (2) below:

$$X-O-(CH_2CH_2CH_2O)_m-(CH_2)_n-A \quad (1)$$

$$X-O-(CH_2-\underset{\underset{R}{|}}{CH}-O)_{m'}-(CH_2)_n-A \quad (2)$$

wherein, X is a polymerizable group having carbon-carbon unsaturated bonds; A is a siloxanyl group; R is H or a methyl group; m is an integer of 1 to 10; m' is an integer of 2 to 10; and n is an integer of 2 to 10.

7 Claims, No Drawings

SILOXANYL-CONTAINING MONOMERS

CROSS REFERENCE TO RELATED APPLICATIONS

This application is a 371 National Stage Entry of PCT International Application No. PCT/JP01/08680, filed Oct. 2, 2001.

TECHNICAL FIELD

This invention relates to monomers, polymers and ophthalmic lenses in which they are used. This invention is particularly suited to use in ophthalmic lenses such as contact lenses, intraocular lenses and artificial corneas.

PRIOR ART

In recent years, 3-methacryloxypropyltris(trimethylsiloxy)silane has been widely used for polymers having high oxygen permeability, and, particular, as a monomer for ophthalmic lenses (Japanese Patent Application Laid-Open No. 60[1985]-142324 and Japanese Patent Application Laid-Open No. 54[1979]-24047). However, because 3-methacryloxypropyltris(trimethylsiloxy) silane has essentially no hydrophilic properties, polymers that are obtained from it have a low water content. This is not desirable for ophthalmic lenses. Further, polymers that are obtained from 3-methacryloxypropyltris(trimethylsiloxy)silane have a comparatively high modulus of elasticity so that it is difficult to use them for soft contact lenses.

A monomer represented by formula (10) below is described in, for example, Japanese Patent Application Laid-Open No. 60[1985]-131518.

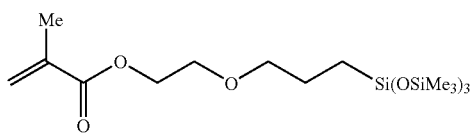
(10)

When the monomer of formula (10) is used, there is a tendency for polymers having higher water content and a lower modulus of elasticity to be obtained than when 3-methacryloxypropyltris(trimethylsiloxy)silane is used. However, this modulus of elasticity is not sufficient and a lower modulus of elasticity is still needed.

DISCLOSURE OF THE INVENTION

This invention has the objective of solving the aforementioned problems and of providing monomers for polymers having high oxygen permeability and also high water content and a low modulus of elasticity. It has the further objective of providing polymers comprised of said monomers, and ophthalmic lenses.

In order to achieve the aforementioned objectives, the monomers and polymers of this invention have the structure indicated below.

[1] A monomer that is represented by formula (1) or (2) below:

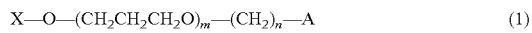
(1)

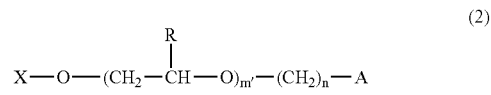
(2)

wherein, X is a polymerizable group having carbon-carbon unsaturated bonds; A is a siloxanyl group; R is H or a methyl group; m is an integer of 1 to 10; m' is an integer of 2 to 10; and n is an integer of 2 to 10.

[2] A polymer comprising the monomer of [1] above as a polymerization component.

EMBODIMENT OF THE INVENTION

We shall now describe the embodiment of this invention. The monomers of this invention are characterized in that they are represented by formula (1) or (2) below:

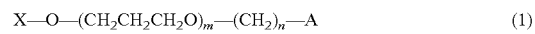
(1)

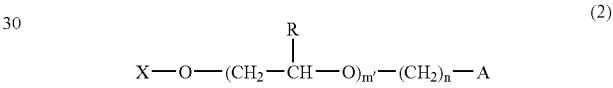
(2)

wherein, X is a polymerizable group having carbon-carbon unsaturated bonds; A is a siloxanyl group; R is H or a methyl group; m is an integer of 1 to 10; m' is an integer of 2 to 10; and n is an integer of 2 to 10.

In this formula, X is a polymerizable group having carbon-carbon unsaturated bonds. Specific examples can include the groups represented by formulas (4) to (9) below. Of these, the groups represented by formulas (4) and (5) are preferable from the standpoints of ease of synthesis and level of polymerization characteristics, and the group represented by formula (5) is the most desirable:

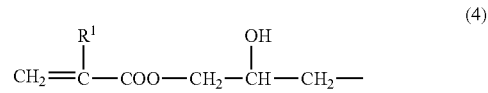
(4)

(5)

(6)

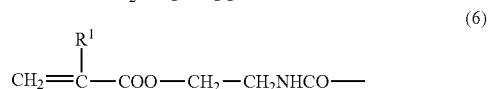
(7)

(8)

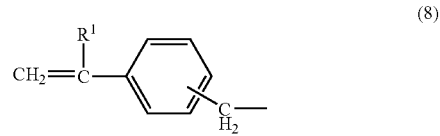

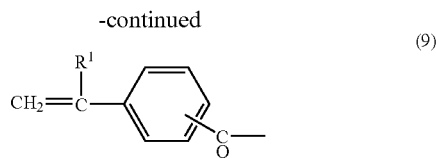
(9)

wherein, in formulas (4) through (9), $R^1$ is H or a methyl group.

In formula (1) or (2), A is a siloxanyl group. The term siloxanyl group in this specification indicates a group that has at least one Si—O—Si bond. Substituents as represented by formula (3) below are desirable for use as siloxanyl groups:

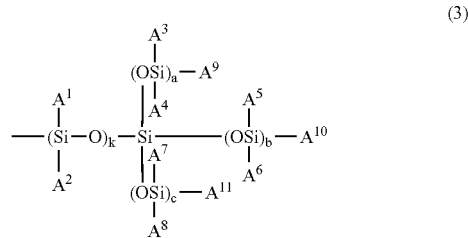
(3)

wherein, in formula (3), $A^1$ to $A^{11}$, respectively and independently, are H, alkyl groups of 1 to 20 carbon atoms that may be substituted or aryl groups of 6 to 20 carbon atoms that may be substituted; k is an integer of 0 to 200; and a, b and c, respectively and independently, are integers of 0 to 20, excepting the case k=a=b=c=0.

In formula (3), $A^1$ to $A^{11}$, respectively and independently, are H, alkyl groups of 1 to 20 carbon atoms that may be substituted or aryl groups of 6 to 20 carbon atoms that may be substituted. Specific examples can include H, alkyl groups such as methyl groups, ethyl groups, propyl groups, isopropyl groups, butyl groups, isobutyl groups, sec-butyl groups, t-butyl groups, hexyl groups, cyclohexyl groups, 2-ethylhexyl groups and octyl groups and aryl groups such as phenyl groups and naphthyl groups. Of these, methyl groups are the most desirable.

In formula (3), k is an integer of 0 to 200, preferably, of 0 to 50, and, more preferably, of 0 to 10. a, b and c are, respectively and independently, integers of 0 to 20, and, preferably, independently and respectively, integers of 0 to 5. When k=0, the combinations of a, b and c should be a=b=c=1, a=b=1 and c=0, and a=1 and b=c=0.

Of the substituents represented by formula (3), those that are particularly desirable because they can be acquired comparatively cheaply on an industrial basis are tris(trimethylsiloxy)siyyl groups, methylbis(trimethylsiloxy)silyl groups, dimethyl(trimethylsiloxy)silyl groups, polydimethylsiloxane groups, polymethylsiloxane groups and poly-co-methylsiloxane-dimethylsiloxane groups.

In formula (1), m is an integer of 1 to 10. However, from the standpoint of balance of the oxygen permeability with high water content and low modulus of elasticity of the polymers obtained from said monomers, m should be 1 or 2, and, most preferably, 1.

Further, in formula (2), m' is an integer of 2 to 10. However, from the standpoint of balance of the oxygen permeability with high water content and low modulus of elasticity of the polymers obtained from said monomers, m' should be 2 or 3, and, most preferably, 2.

In formulas (1) and (2), n is an integer of 2 to 10. From the standpoint of ease of synthesis, n should be 2 or 3, and, most preferably, 3.

The following method can be presented as an example of the method of synthesis of the monomers represented by formula (1). First, a compound represented by formula (II):

(11)

wherein, in formula (11), m is an integer of 1 to 10 and R is H or a methyl group, is reacted with a compound represented by formula (12):

(12)

wherein, in formula (12), Z is elimination groups such as I, Br, Cl and p-toluenesulfonyloxy groups and n is an integer of 2 to 10, in the presence of a base such as potassium hydroxide or sodium hydride, to obtain a compound as represented by formula (13):

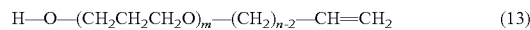
(13)

wherein, in formula (13), m is an integer of 1 to 10, n is an integer of 2 to 10, and R is H or a methyl group.

Then, by reacting the compound represented by formula (13) with a suitable compound having carbon-carbon unsaturated bonds, a compound represented by formula (14)

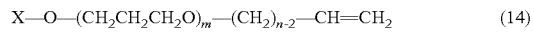
(14)

is obtained. The suitable compound having carbon-carbon unsaturated bonds differs depending on the type of X. For example, when X is a group represented by formula (4), it is the corresponding epoxy compound, when X are groups represented by formula (5), formula (8) and formula (9), it is the corresponding halide and when X are groups represented by formula (6) and formula (7), it is the corresponding isocyanate compound. Next, a compound as represented by formula (14) is reacted with a compound as represented by formula (15)

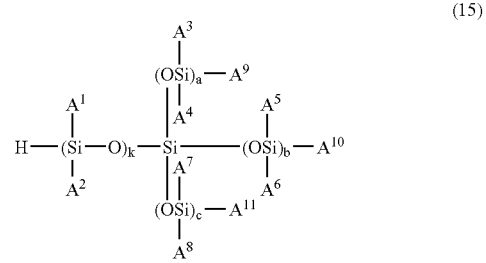
(15)

in the presence of a hydrosilylated catalyst of which platinum systems are represented, with a monomer as represented by formula (1) being obtained. At this time, a chlorosilane compound can be used instead of the compound represented by formula (15). When a chlorosilane compound is used, the monomer represented by formula (1) can be obtained by condensing the chlorosilane addition product that is obtained with an alkoxysilane compound or a chlorosilane compound in the presence of water.

Further, the following method can be presented as an example of the synthesis of monomers represented by formula (2). First, a compound represented by formula (16):

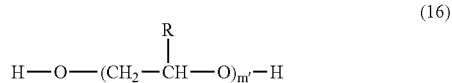

(16)

wherein, in formula (16), R is H or a methyl group and m' is an integer or 2 to 10, is reacted with a compound represented by the aforementioned formula (12), in the presence of a base such as potassium hydroxide or sodium hydride, and a compound represented by formula (17) is obtained:

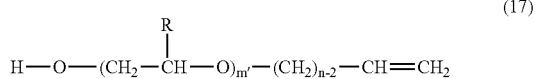

(17)

wherein, in formula (17), R is H or a methyl group, m' is an integer of 2 to 10, and n is an integer of 2 to 10.

Next, the compound represented by formula (17) is reacted with a suitable compound having carbon-carbon unsaturated bonds, by which means a compound represented by formula (18) is obtained.

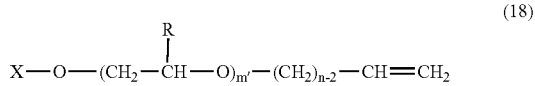

(18)

The suitable compound having carbon-carbon unsaturated bonds differs depending on the type of X. For example, when X is a group represented by formula (4), it is the corresponding epoxy compound, when X are groups represented by formula (5), formula (8) and formula (9), it is the corresponding halide and when X are groups represented by formula (6) and formula (7), it is the corresponding isocyanate compound. Next, the compound represented by formula (18) is reacted with the compound represented by the aforementioned formula (15) in the presence of a hydrosilylated catalyst of which platinum systems are representatives, and a monomer as represented by formula (2) is obtained. At this time, a chlorosilane compound can be used instead of the compound represented by formula (15). When a chlorosilane compound is used, the monomer represented by formula (2) can be obtained by condensing the chlorosilane addition product that is obtained with an alkoxysilane compound or a chlorosilane compound in the presence of water.

The polymers of this invention can be obtained by polymerizing the monomers represented by formulas (1) or (2) individually or they can be obtained by copolymerization with other monomers. In the case of copolymerization with other monomers, there are no particular limitations on the copolymerization monomers as long as they can be copolymerized, and monomers having (meth)acryloyl groups, styryl groups, allyl groups, vinyl groups and other copolymerizable carbon-carbon unsaturated bonds can be used.

We shall now present several examples of suitable other monomers. However, they are not limited to these examples. They can include (meth)acrylic acid, itaconic acid, crotonic acid, cinnamic acid, vinyl benzoic acid; alkyl(meth)acrylates such as methyl (meth)acrylate and ethyl(meth)acrylate; polyfunctional (meth)acrylates such as polyalkylene glycol mono(meth)acrylate, polyalkylene glycolmonoalkyl ether (meth)acrylate, polyalkylene glycol bis(meth)acrylate, trimethylolpropanetris(meth)acrylate, pentaerythritoltetrakis (meth)acrylate and siloxane macromers having carbon-carbon unsaturated bonds in both terminals; halogenated alkyl(meth)acrylates such as trifluoroethyl(meth)acrylate and hexafluoroisopropyl(meth)acrylate; hydroxyalkyl(meth) acrylates having hydroxy groups such as 2-hydroxyethyl (meth)acrylate and 2,3-dihydroxypropyl(meth)acrylate; (meth)acrylamides such as N,N-dimethyl acrylamide, N,N-diethyl acrylamide, N,N-di-n-propyl acrylamide, N,N-diisopropyl acrylamide, N,N-di-n-butyl acrylamide, N-acryloyl morpholine, N-acryloyl piperidine, N-acryloyl pyrrolidine and N-methyl(meth)acrylamide; aromatic vinyl monomers such as styrene, α-methylstyrene and vinyl pyridine; maleimides; heterocyclic vinyl monomers such as N-vinyl pyrrolidone, N-vinyl caprolactam, N-vinyl oxasolidone, 1-vinyl imidazole, N-vinyl carbazole, vinyl pyridine and vinyl pyrazine; N-vinyl carboxamides such as N-vinyl formamide, N-vinyl acetamide and N-methyl-N-vinyl acetamide; vinyl esters such as vinyl acetate; 3-[tris(trimethylsiloxy)silyl] propyl(meth)acrylate, 3-[bis(trimethylsiloxy)methylsilyl] propyl(meth)acrylate, 3-[(trimethylsiloxy)dimethylsilyl] propyl(meth)acrylate, 3-[tris(trimethylsiloxy)silyl]propyl (meth)acrylamide, 3-[bis(trimethylsiloxy)methylsilyl] propyl(meth)acrylamide, 3-[(trimethylsiloxy)dimethylsilyl] propyl(meth)acrylamide, [tris(trimethylsiloxy)silyl]methyl (meth)acrylate, [bis(trimethylsiloxy)methylsilyl]methyl (meth)acrylate, [(trimethylsiloxy)dimethylsilyl]methyl (meth)acrylate, [tris(trimethylsiloxy)silyl]methyl(meth) acrylamide, [bis(trimethylsiloxy)methylsilyl]methyl(meth) acrylamide, [(trimethylsiloxy)dimethylsilyl]methyl(meth) acrylamide, [tris(trimethylsiloxy)silyl]styrene, [bis (trimethylsiloxy)methylsilyl]styrene, [(trimethylsiloxy) dimethylsilyl]styrene, N-[3-[tris(trimethylsiloxy)silyl] propyl]vinyl carbamide, N-[3-[bis(trimethylsiloxy) methylsilyl]propyl]vinyl carbamide, N-[3-[(trimethylsiloxy) dimethylsilyl]propyl]vinyl carbamide and compounds of formulas (19) to (21) indicated below:

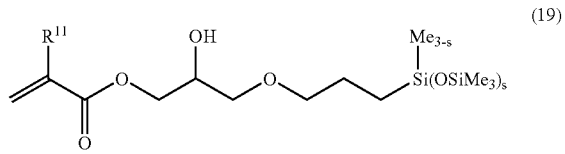

(19)

(20)

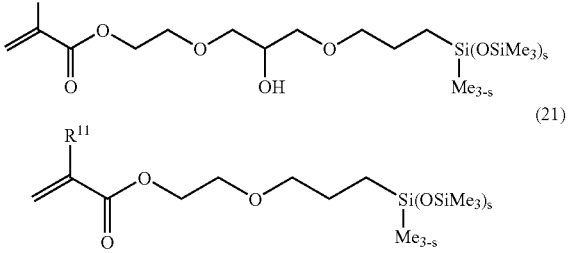

(21)

wherein, in formulas (19) to (21), $R^{11}$ is H or a methyl group and s is an integer of 1 to 3.

For the purpose of obtaining good mechanical properties and of obtaining good resistance to disinfecting solutions and washing solutions, in the polymer of this invention, it is desirable to use monomers having two or more copolymerizable carbon-carbon unsaturated bonds in one molecule as copolymerization components. The copolymerization ratio of monomers having two or more copolymerizable carbon-carbon unsaturated bonds in one molecule should be 0.1 weight % to 70 weight %, and, preferably, 0.2 weight % to 40 weight %.

From the standpoint of achieving both high oxygen permeability and high water content, it is desirable to copolymerize and use monomers represented by formula (1) or (2) for the polymers of this invention. In this case, the copolymerization ratio of monomers represented by formula (1) or (2) should be 30 weight % to 97 weight %, preferably, 50 weight % to 95 weight %, and, more preferably, 60 weight % to 90 weight %. When the copolymerization ratio of the monomers represented by formula (1) or (2) is too low, oxygen permeability of the polymer is decreased. When it is too high, there is a tendency for water content to decrease.

The polymers of this invention may also contain ultraviolet absorbents, pigments and colorants. Ultraviolet absorbents, pigments and colorants having polymerizable groups may also be present in copolymerized form.

When the polymers of this invention are obtained by (co)polymerization, thermal polymerization initiators and photopolymerization initiators, of which peroxides and azo compounds are representative, may be added to facilitate polymerization. When thermal polymerization is performed, substances having optimum dissolution properties at the desired reaction temperature are selected and used. In general, azo initiators and peroxide initiators having 10 hours half-life temperatures of 40 to 120° C. are desirable. Carbonyl compounds, peroxides, azo compounds, sulfur compounds, halides and metal salts can be cited as photopolymerization initiators. These polymerization initiators can be used individually or in mixtures and are used in quantities up to about 1 weight %.

Polymerization solvents can be used when the polymers of this invention are obtained by (co)polymerization. Various organic and inorganic solvents can be used as solvents and there are no particular limitations on them. Examples that can be cited include water, alcohol solvents such as methyl alcohol, ethyl alcohol, normal propyl alcohol, isopropyl alcohol, normal butyl alcohol, isobutyl alcohol and tert-butyl alcohol; glycol ether solvents such as methyl cellosolve, ethyl cellosolve, isopropyl cellosolve, butyl cellosolve, propylene glycol monomethyl ether, ethylene glycol dimethyl ether, diethylene glycol dimethyl ether and triethylene glycol dimethyl ether; ester solvents such as ethyl acetate, butyl acetate, amyl acetate, ethyl lactate and methyl benzoate; aliphatic hydrocarbon solvents such as normal hexane, normal heptane and normal octane; alicyclic hydrocarbon solvents such as cyclohexane and ethyl cyclohexane; ketone solvents such as acetone, methyl ethyl ketone and methyl isobutyl ketone; aromatic hydrocarbon solvents such as benzene, toluene and xylene; and petroleum solvents. They can be used individually or in mixtures.

Known polymerization methods and molding methods can be used for the polymers of this invention. For example, there is a method in which they are polymerized and molded into rods or plates and are processed to the desired shapes by cutting and processing, a mold polymerization method and a spin cast polymerization method.

As an example, we shall now describe the case in which the polymers of this invention are obtained by the mold polymerization method.

A monomer composition is filled into the space of two molds having a fixed shape. Photopolymerization or thermal polymerization is performed and it is formed to the shape of the mold. The mold can be made of resin, glass, ceramics or metal. In the case of photopolymerization, a material that is optically transparent is used, and, ordinarily, resin or glass is used. In many cases, when the polymer is manufactured, a space is formed by the two opposing molds and the space is filled with the monomer composition. Depending on the shape of the mold and the properties of the monomer, a gasket may be used for the purpose of conferring a fixed thickness on the polymer and of preventing leakage of the filled monomer composition. The mold into the space of which the monomer composition is filled, is then irradiated with active light rays such as ultraviolet rays or is introduced into an oven or water bath or oil bath to heat and polymerize. The two methods can also be used in combination, with thermal polymerization being performed after photopolymerization, or, conversely, photopolymerization can be performed after thermal polymerization. In the case of photopolymerization, for example, light containing a large portion of ultraviolet rays is usually irradiated for a short time (ordinarily 1 hour or less) using a mercury lamp or an insect attraction lamp as the light source. When thermal polymerization is performed, the temperature is gradually raised from close to room temperature, being increased to a temperature of 60° C. to 200° C. over a period of several hours to several tens of hours. These conditions are desirable for the purpose of maintaining the optical homogeneity and quality of the polymer and of increasing reproducibility.

The polymers of this invention can be subjected to modification treatments by various methods. It is desirable to perform said modification treatments for the purpose of increasing surface wettability.

Specific modification methods of polymers can include electromagnetic waves (including light) irradiation, plasma irradiation, chemical vapor deposition treatments such as vaporization and sputtering, heating, treatment with bases, treatment with acids and the use of other suitable surface treatment agents, and combinations of these treatments. Of these modification procedures, treatment with bases and treatment with acids are desirable because they are simple.

Examples of treatments with bases or treatments with acids that can be cited include a method in which the polymer is brought into contact with a basic or acidic solution and a method in which the polymer is brought into contact with a basic or acidic gas. More specific examples of these methods include, for example, methods in which the polymer is immersed in a basic or acidic solution, methods in which a basic or acidic solution or basic or acidic gas is sprayed at the polymer, methods in which the basic or acidic solution is applied to the polymer with a spatula or brush and methods in which the basic or acidic solution is applied to the polymer by a spin coating method or a dip coating method. The method whereby great modifying effects can be obtained most simply is the method in which the polymer is immersed in the basic or acidic solution.

There are no particular limitations on temperature when the polymer is immersed in the basic or acidic solution. However, the procedure is usually performed in a temperature range of approximately −50° C. to 300° C. When workability is considered, a temperature range of −10° C. to 150° C. is preferable and −5° C. to 60° C. is more preferable.

The optimum period for immersion of the polymer in the basic or acidic solution varies depending on the temperature. In general, a period of up to 100 hours is desirable, a period of up to 24 hours is more preferable and a period of up to 12 hours is most preferable. When contact time is too long, workability and productivity deteriorate and there are instances in which there are such deleterious effects as decrease of oxygen permeability and decrease of mechanical properties.

The bases that can be used include alkali metal hydroxides, alkaline earth metal hydroxides, various carbonates, various borates, various phosphates, ammonia, various ammonium salts, various amines and high molecular weight bases such as polyethylene imines and polyvinyl amines. Of these, alkali metal hydroxides are the most desirable because they are inexpensive and very effective.

The acids that can be used include various inorganic acids such as sulfuric acid, phosphoric acid, hydrochloric acid and nitric acid, various organic acids such as acetic acid, formic acid, benzoic acid and phenol and high molecular weight acids such as polyacrylic acids, polymethacrylic acids, polystyrene sulfonic acids and polysulfomethyl styrene. Of these, high molecular weight acids are the most desirable because of their great treatment effectiveness and little deleterious effect on other physical properties.

Various inorganic and organic solvents can be used as solvents of the basic or acidic solution. For example, they can include water; various alcohols such as methanol, ethanol, propanol, 2-propanol, butanol, ethylene glycol, diethylene glycol, triethylene glycol, tetraethylene glycol, polyethylene glycol and glycerol; various aromatic hydrocarbons such as benzene, toluene and xylene; various aliphatic hydrocarbons such as hexane, heptane, octane, decane, petroleum ether, kerosene, ligroin and paraffin; various ketones such as acetone, methyl ethyl ketone and methyl isobutyl ketone; various esters such as ethyl acetate, butyl acetate, methyl benzoate and dioctyl phthalate; various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether; various nonprotonic polar solvents such as dimethylformamide, dimethylacetamide, N-methyl-2-pyrrolidone, dimethylimidazolidinone, hexamethyl phosphoric triamide and dimethyl sulfoxide; halogen solvents such as methylene chloride, chloroform, dichloroethane trichloroethane and trichloroethylene; and freon solvents. Of these, water is the most desirable from the standpoints of economic factors, convenience of handling and chemical stability. These solvents can also be used in mixtures of two or more.

The basic or acidic solutions that are used in this invention may also contain components other than the basic substances or acidic substances and the solvents.

In this invention, after the polymer has been subjected to treatment with a base or an acid, the basic or acidic substance can be removed by washing.

Various inorganic and organic solvents can be used as washing solvents. For example, they can include water; various alcohols such as methanol, ethanol, propanol, 2-propanol, butanol, ethylene glycol, diethylene glycol, triethylene glycol, tetraethylene glycol, polyethylene glycol and glycerol; various aromatic hydrocarbons such as benzene, toluene and xylene; various aliphatic hydrocarbons such as hexane, heptane, octane, decane, petroleum ether, kerosene, ligroin and paraffin; various ketones such as acetone, methyl ethyl ketone and methyl isobutyl ketone; various esters such as ethyl acetate, butyl acetate, methyl benzoate and dioctyl phthalate; various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether; various nonprotonic polar solvents such as dimethylformamide, dimethylacetamide, N-methyl-2-pyrrolidone, dimethylimidazolidinone, hexamethyl phosphoric triamide and dimethyl sulfoxide; halogen solvents such as methylene chloride, chloroform, dichloroethane trichloroethane and trichloroethylene; and freon solvents. Generally, water is the most desirable.

Mixtures of two or more of these solvents can be used as the washing solvent. The washing solvent may also contain components other than the solvents, for example, inorganic salts, surfactants and detergents.

The entire polymer may be subjected to said modification treatment or it may be performed on only a portion of the polymer, for example, the surface. When only the surface is subjected to modification treatment, wettability of the surface can be improved without making great changes in the polymer as a whole.

The oxygen permeability coefficient of the polymer of this invention should be greater than $50\times10^{-11}$ $(cm^2/sec)[mLO_2/(mL \cdot hPa)]$, preferably, greater than $55\times10^{-11}$ $(cm^2/sec)[mLO_2/(mL \cdot hPa)]$, and, most preferably, greater than $60\times10^{-11}$ $(cm^2/sec)[mLO_2/(mL \cdot hPa)]$ in terms of the oxygen permeability. By setting the oxygen permeability coefficient in this range, the burden on the eyes can be decreased and continuous wearing is facilitated when used as contact lenses.

The water content should be 15 weight % to 60 weight %, preferably, 20 weight % to 55 weight %, and, more preferably, 25 weight % to 50 weight %. When the water content is greater than 15 weight %, its action in the eyes is improved when used as a contact lens and continuous wearing is facilitated. When the water content is excessively high, the oxygen permeability coefficient is decreased, for which reason this is not desirable.

The modulus of elasticity should be 65 kPa to 2000 kPa, preferably, 100 kPa to 1400 kPa, and, most preferably, 150 kPa to 850 kPa. When the modulus of elasticity is excessively low, the polymer is too soft, so that its shape-maintaining capacity deteriorates and it is difficult to handle, for which reason this is not desirable. When the modulus of elasticity is excessively high, the polymer is excessively hard and, when it is used as a contact lens, comfort on wearing deteriorates, for which reason this is not desirable.

The monomers and polymers of this invention are particularly suited for ophthalmic lenses such as contact lenses, intraocular lenses and artificial corneas.

We shall now describe this invention in specific terms by means of examples. However, this invention is not limited by them.

Determination Methods

The various determinations in these examples were performed by the methods described below.

(1) Proton Nuclear Magnetic Resonance Spectrum

Determinations were performed using Model EX270 manufactured by JEOL Ltd. Chloroform-d was used as the solvent. The chloroform peak was taken as the internal standard (7.26 ppm).

(2) Oxygen Permeability Coefficient

The oxygen permeability coefficient of a sample in the shape of a contact lens was determined in water of 35° C. using a Seikaken-shiki film oxygen permeability meter manufactured by RIKA SEIKI KOGYO Co., Ltd. The film thickness of the sample was controlled according to necessity by overlapping plurality of films.

(3) Water Content

A sample in the form of a contact lens was used. The sample was dried for 16 hours at 40° C. in a vacuum dryer and the weight (Wd) of the sample was determined. Following that, it was immersed in pure water and was impregnated with water overnight in a constant temperature tank at 40° C., after which the water on the surface was wiped off with Kimwipe and its weight (Ww) was measured. The water content was found by the following formula.

Water content(%)=100×(Ww−Wd)/Ww (4) Modulus of Elasticity

A sample [width (smallest part), 5 mm; length, 14 mm; thickness, about 0.2 mm] cut from a substance in the contact lens shape using a stipulated punch mold was used, and determinations were made using Model RTM-100 TENSILON manufactured by Orientec Corporation. The drawing rate was set to 100 mm/min and the distance between grips was set to 5 mm.

EXAMPLE 1

Synthesis of the Compound Represented by Formula (22)

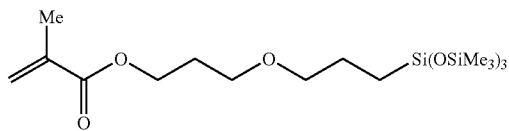
(22)

(1) 1,3-propanediol (100 g) and potassium hydroxide (86.7 g) were introduced into a 500 mL three-neck distillation flask equipped with a dropping funnel, a reflux condenser and a stirring blade, and the mixture was stirred for about 1 hour at room temperature. Allyl bromide (159 g) was introduced through the dropping funnel and was added dropwise while the mixture was being stirred. After the dropwise addition had been completed, a reaction was carried out for 3 hours at 60° C. as the mixture was being stirred. Diethyl ether (250 mL) was added, after which the salt was removed by filtration and the solvent component was removed with a rotary vacuum evaporator. Because the salt again precipitated, it was removed by filtration. Purification was performed by distillation under reduced pressure and 3-allyloxypropanol was obtained as a colorless, transparent liquid.

(2) The 3-allyloxypropanol (15 g) that was synthesized in (1), triethylamine (19.6 g) and tetrahydrofuran (30 mL) were introduced into a 300 mL three-neck distillation flask equipped with a dropping funnel and a stirring blade. The three neck distillation flask was immersed in an ice bath and methacrylic acid chloride (20.2 g) was added dropwise over a period of approximately 30 minutes as the mixture was being stirred. After the dropwise addition was completed, stirring was continued for 2 hours at room temperature. The salt that precipitated was removed by suction and filtration. Ethyl acetate (100 mL) was added to the filtrate which was then introduced into a separatory funnel and washed using a saline solution, saturated aqueous solution of sodium hydrogen carbonate and saline solution in that order. Dehydration treatment was performed with anhydrous magnesium sulfate, after which the solvent was removed with a rotary vacuum evaporator. Purification was performed by distillation under reduced pressure and 3-allyloxypropyl methacrylate was obtained as a colorless, transparent liquid.

(3) Chloroplatinic acid 6-hydrate was dissolved in an equal volume of 2-propanol and was diluted to $1.93 \times 10^{-5}$ mol/g with tetrahydrofuran. Hereafter, this solution is called the "catalyst solution."

The 3-allyloxypropyl methacrylate (6.94 g) that was synthesized in (2), toluene (12 g) and the catalyst solution (3.9 g) were introduced into a 100 mL eggplant type flask equipped with a magnetic rotor. The flask was immersed in a water bath and was cooled, and trichlorosilane (10.21 g) was added in small amounts at a time as the mixture was being stirred. After it was confirmed that generation of heat stopped, the flask was hermetically sealed with a septum and was allowed to stand overnight at room temperature. The low boiling point components were removed by means of a rotary vacuum evaporator, after which purification was performed by distillation under reduced pressure and 3-(3-methacryloxypropoxy) propyl trichlorosilane was obtained as a colorless, transparent liquid.

(4) Hexane (2.4 g), methanol (2.4 g), and water (4.8 g) were introduced into a 200 mL eggplant type flask equipped with a magnetic rotor, the flask was immersed in an ice bath and the contents of the flask were stirred vigorously. A mixture consisting of the 3-(3-methacryloxypropoxy)propyl trichlorosilane (4.58 g) synthesized in (3) and methoxytrimethyl silane (8.94 g) was added dropwise over a period of approximately 10 minutes. After the dropwise addition was completed, stirring was continued for 4 hours at room temperature. The reaction solution was separated into two layers and the top layer was collected with a separatory funnel. It was washed using a saturated aqueous solution of sodium hydrogen carbonate (3 times) and water (2 times) in that order. Dehydration was performed with anhydrous sodium sulfate, after which the solvent was removed with a rotary vacuum evaporator. Purification was performed by distillation under reduced pressure and a pale yellow transparent liquid was obtained. The proton nuclear magnetic resonance spectrum of this liquid was determined and analyzed. As a result, peaks were detected in the vicinity of 0.1 ppm (27H), in the vicinity of 0.4 ppm (2H), in the vicinity of 1.6 ppm (2H), in the vicinity of 1.9 ppm (5H), in the vicinity of 3.3 ppm (2H), in the vicinity of 3.5 ppm (2H), in the vicinity of 4.2 ppm (2H), in the vicinity of 5.5 ppm (1H) and in the vicinity of 6.1 ppm (1H). From these findings, it was confirmed that this was the compound represented by formula (22).

EXAMPLE 2

Synthesis of the Compound Represented by Formula (23)

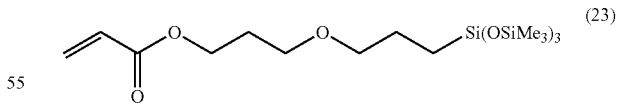
(23)

A pale yellow transparent liquid was obtained in the same way as in Example 1 except that acrylic acid chloride was used instead of methacrylic acid chloride. The proton nuclear magnetic resonance spectrum of this liquid was determined and analyzed. As a result, peaks were detected in the vicinity of 0.1 ppm (27H), in the vicinity of 0.4 ppm (2H), in the vicinity of 1.6 ppm (2H), in the vicinity of 1.9 ppm (2H), in the vicinity of 3.3 ppm (2H). in the vicinity of 3.5 ppm (2H), in the vicinity of 4.2 ppm (2H), in the vicinity of 5.8 ppm (1H), in the vicinity of 6.2 ppm (1H) and in the vicinity of 6.4 ppm (1H). From these findings, it was confirmed that this was the compound represented by formula (23).

EXAMPLE 3

The compound of formula (22) (65 parts by weight) obtained in Example 1, N,N-dimethyl acrylamide (35 parts by weight), triethylene glycol dimethacrylate (1 part by weight), Darocure 1173 (manufactured by CIBA Specialty Chemicals Inc., 0.5 part by weight) and diethylene glycol dimethyl ether (10 parts by weight) were mixed and stirred. A homogeneous, transparent monomer mixture was obtained, and this monomer mixture was deaerated in an argon atmosphere. It was poured into a contact lens mold made of transparent resin (poly 4-methylpentene-1) in a glove box in a nitrogen atmosphere, polymerization was performed by irradiation (1 mW/cm$^2$, 10 minutes) using an insect attraction lamp, and a contact lens-shaped sample was obtained. It was immersed for 16 hours at 60° C. in a large excess volume of isopropyl alcohol, after which it was immersed for 24 hours in a large excess volume of pure water. Following that, it was immersed and stored in clear, pure water. The sample that was obtained was transparent and was not turbid. The oxygen permeability coefficient of this sample was $70\times10^{-11}$ (cm$^2$/sec) [mLO$_2$/(mL·hPa)], its water content was 30% and its modulus of elasticity was 380 kPa. Thus, it had high oxygen permeability, high water content and a low modulus of elasticity.

EXAMPLE 4

A contact lens-shaped sample was obtained in the same way as in Example 3 except that the compound of formula (23) (35 parts by weight) obtained in Example 2 and 3-methacryloxypropyltris(trimethylsiloxy)silane (30 parts by weight) were used instead of the compound of formula (22) (65 parts by weight). The sample that was obtained was transparent and was not turbid. The oxygen permeability coefficient of this sample was $75\times10^{-11}$ (cm$^2$/sec) [mLO$_2$/(mL·hPa)], its water content was 26% and its modulus of elasticity was 280 kPa. Thus, it had high oxygen permeability, high water content and a low modulus of elasticity.

EXAMPLE 5

Synthesis of the Compound Represented by Formula (24)

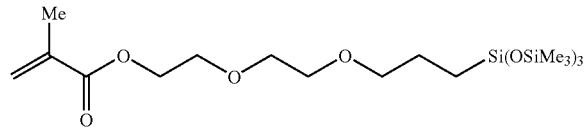

(24)

(1) Diethylene glycol (100 g) and potassium hydroxide (62.2 g) were introduced into a 500 mL three-neck distillation flask equipped with a dropping funnel, a reflux condenser and a stirring blade, and the mixture was stirred for about 1 hour at room temperature. Allyl bromide (114 g) was introduced through the dropping funnel and was added dropwise while the mixture was being stirred. After the dropwise addition had been completed, a reaction was carried out for 3 hours at 60° C. as the mixture was being stirred. Diethyl ether (250 mL) was added, after which the salt was removed by filtration and the solvent component was removed with a rotary vacuum evaporator. Because the salt again precipitated, it was removed by filtration. Purification was performed by distillation under reduced pressure, and diethylene glycol monoallyl ether was obtained as a colorless, transparent liquid.

(2) The diethylene glycol monoallyl ether (20 g) that was synthesized in (1), triethylamine (20.7 g) and tetrahydrofuran (30 mL) were introduced into a 300 mL three-neck distillation flask equipped with a dropping funnel and a stirring blade. The three-neck distillation flask was immersed in an ice bath and methacrylic acid chloride (21.4 g) was added dropwise over a period of approximately 5 minutes as the mixture was being stirred. After the dropwise addition was completed, stirring was continued for 3 hours at room temperature. The salt that precipitated was removed by suction and filtration. Ethyl acetate (100 mL) was added to the filtrate which was then introduced into a separatory funnel and was washed using a saline solution, saturated aqueous solution of sodium hydrogen carbonate and saline solution in that order. Dehydration treatment was performed with anhydrous magnesium sulfate, after which the solvent was removed with a rotary vacuum evaporator. Purification was performed by distillation under reduced pressure and 2-(2-allyloxyethoxy)ethyl methacrylate was obtained as a colorless, transparent liquid.

(3) The 2-(2-allyloxyethoxy)ethyl methacrylate (13.63 g) that was synthesized in (2), toluene (13 g) and the catalyst solution (6.6 g) were introduced into a 100 mL eggplant type flask equipped with a magnetic rotor. The flask was immersed in a water bath and was cooled, and trichlorosilane (17.22 g) was added in small amounts at a time as the mixture was being stirred. After it was confirmed that generation of heat stopped, the flask was hermetically sealed with a septum and was allowed to stand overnight at room temperature. The low boiling point components were removed by means of a rotary vacuum evaporator, after which purification was performed by distillation under reduced pressure and 3-[2-(2-methacryloxyethoxy)ethoxy]propyl trichlorosilane was obtained as a colorless, transparent liquid.

(4) Hexane (6.0 g), methanol (6.0 g) and water (12.0 g) were introduced into a 200 mL eggplant type flask equipped with a magnetic rotor, the flask was immersed in an ice bath and the contents of the flask were stirred vigorously. A mixture consisting of 3-[2-(2-methacryloxyethoxy)ethoxy]propyl trichlorosilane (12.5 g) and methoxytrimethyl silane (22.3 g) was added dropwise over a period of approximately 10 minutes. After the dropwise addition was completed, stirring was continued for 3.5 hours at room temperature. The reaction solution was separated into two layers and the top layer was collected with a separatory funnel. It was washed using a saturated aqueous solution of sodium hydrogen carbonate (3 times) and water (2 times) in that order. Dehydration was performed with anhydrous sodium sulfate, after which the solvent was removed with a rotary vacuum evaporator. Purification was performed by distillation under reduced pressure and a pale yellow transparent liquid was obtained. The proton nuclear magnetic resonance spectrum of this liquid was determined and analyzed. As a result, peaks were detected in the vicinity of 0.1 ppm (27H), in the vicinity of 0.4 ppm (2H), in the vicinity of 1.6 ppm (2H), in the vicinity of 1.9 ppm (3H), in the vicinity of 3.4 ppm (2H), in the vicinity of 3.5 to 3.8 ppm (6H), in the vicinity of 4.3 ppm (2H), in the vicinity of 5.5 ppm (1H) and in the vicinity of 6.1 ppm (1H). From these findings, it was confirmed that this was the compound represented by formula (24).

EXAMPLE 6

Synthesis of the Compound Represented by Formula (25)

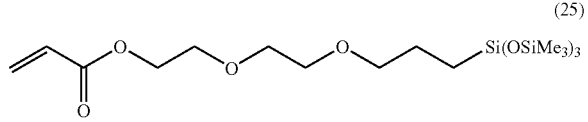

(25)

A pale yellow transparent liquid was obtained in the same way as in Example 1 except that acrylic acid chloride was used instead of methacrylic acid chloride. The proton nuclear magnetic resonance spectrum of this liquid was determined and analyzed. As a result, peaks were detected in the vicinity of 0.1 ppm (27H), in the vicinity of 0.4 ppm (2H), in the vicinity of 1.6 ppm (2H), in the vicinity of 3.4 ppm (2H), in the vicinity of 3.5 to 3.8 ppm (6H), in the vicinity of 4.3 ppm (2H), in the vicinity of 5.8 ppm (1H), in the vicinity of 6.2 ppm (1H) and in the vicinity of 6.4 ppm (1H). From these findings, it was confirmed that this was the compound represented by formula (25).

EXAMPLE 7

The compound of formula (24) (65 parts by weight) obtained in Example 1, N,N-dimethyl acrylamide (35 parts by weight), triethylene glycol dimethacrylate (1 part by weight), Darocure 1173 (manufactured by CIBA Specialty Chemicals Inc., 0.5 part by weight) and diethylene glycol dimethyl ether (10 parts by weight) were mixed and stirred. A homogeneous, transparent monomer mixture was obtained. This monomer mixture was deaerated in an argon atmosphere. It was then poured into a contact lens mold made of transparent resin (poly 4-methylpentene-1) in a glove box in a nitrogen atmosphere, polymerization was performed by irradiation (1 mW/cm$^2$, 10 minutes) using an insect attraction lamp, and a contact lens-shaped sample was obtained. It was immersed for 16 hours at 60° C. in a large excess volume of isopropyl alcohol, after which it was immersed for 24 hours in a large excess volume of pure water. Following that, it was immersed and stored in clear, pure water. The sample that was obtained was transparent and was not turbid. The oxygen permeability coefficient of this sample was $69 \times 10^{-11}$ (cm$^2$/sec) [mLO$_2$/(mL·hPa)], its water content was 39% and its modulus of elasticity was 180 kPa. Thus, it had high oxygen permeability, high water content and a low modulus of elasticity.

EXAMPLE 8

A contact lens-shaped sample was obtained in the same way as in Example 7 except that the compound of formula (25) (35 parts by weight) obtained in Example 2 and 3-methacryloxypropyltris(trimethylsiloxy)silane (30 parts by weight) were used instead of the compound of formula (24) (65 parts by weight). The sample that was obtained was transparent and was not turbid. The oxygen permeability coefficient of this sample was $74 \times 10^{-11}$ (cm$^2$/sec) [mLO$_2$/(mL·hPa)], its water content was 38% and its modulus of elasticity was 280 kPa. Thus, it had high oxygen permeability, high water content and a low modulus of elasticity.

COMPARATIVE EXAMPLE 1

A contact lens-shaped sample was obtained in the same way as in Example 3 except that 3-methacryloxypropyltris (trimethylsiloxy)silane (65 parts by weight) was used instead of the compound of formula (22) (65 parts by weight). The sample that was obtained was transparent and was not turbid. The oxygen permeability coefficient of this sample was $83 \times 10^{-11}$ (cm$^2$/sec) [mLO$_2$/(mL·hPa)], its water content was 22% and its modulus of elasticity was 2050 kPa. Although it had high oxygen permeability, its water content was lower and its modulus of elasticity was higher than in Example 3, Example 4, Example 7 and Example 8.

COMPARATIVE EXAMPLE 2

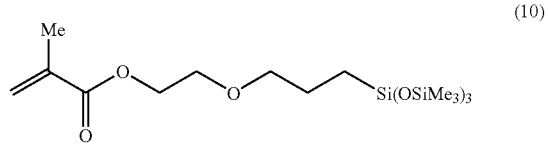

(10)

A contact lens-shaped sample was obtained in the same way as in Example 3 except that the compound represented by formula (10) (65 parts by weight) was used instead of the compound of formula (22) (65 parts by weight). The sample that was obtained was transparent and was not turbid. The oxygen permeability coefficient of this sample was $71 \times 10^{-11}$ (cm$^2$/sec) [mLO$_2$/(mL·hPa)], its water content was 25% and its modulus of elasticity was 830 kPa. Although it had high oxygen permeability and a high water content, its modulus of elasticity was higher than in Example 3, Example 4, Example 7 and Example 8.

INDUSTRIAL APPLICABILITY

By means of monomers of this invention, polymers and ophthalmic lenses having high oxygen permeability, high water content and a low modulus of elasticity are obtained.

The invention claimed is:

1. A monomer that is represented by formula (1) or (2) below:

X—O—(CH$_2$CH$_2$CH$_2$O)$_m$—(CH$_2$)$_n$—A (1)

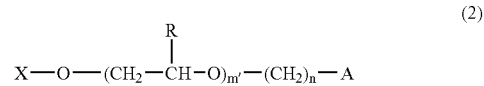

(2)

wherein, A is a siloxanyl group; R is H or a methyl group; m is an integer of 1 to 10; m' is an integer of 2 to 10; and n is an integer of 2 to 10 and X is one substituent selected from substituents as represented by formulas (4) to (9) below:

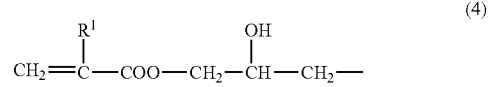

(4)

-continued

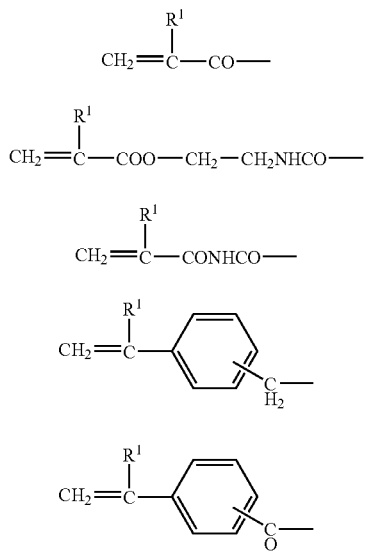

wherein, in formulas (4) to (9), $R^1$ is H or a methyl group.

2. The monomer of claim 1 wherein the aforementioned siloxanyl group is a substituent as represented by formula (3) below:

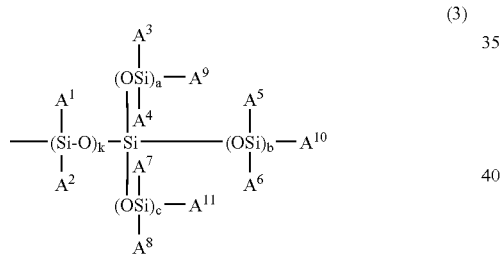

wherein, in formula (3), $A^1$ to $A^{11}$, respectively and independently, are H, alkyl groups of 1 to 20 carbon atoms that may be substituted or aryl groups of 6 to 20 carbon atoms that may be substituted; k is an integer of 0 to 200; and a, b and c, respectively and independently, are integers of 0 to 20, excepting the case k=a=b=c=0.

3. A monomer that is represented by formula (1) or (2) below:

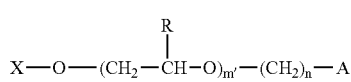

wherein, X is a polymerizable group having carbon-carbon unsaturated bonds; A is a siloxanyl group; R is a methyl group; m is an integer of 1 to 10; m' is an integer of 2 to 10; and n is an integer of 2 to 10.

4. The monomer of claim 3 wherein the aforementioned siloxanyl group is a substituent as represented by formula (3) below:

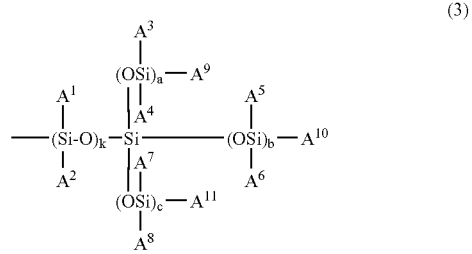

wherein, in formula (3), $A^1$ to $A^{11}$, respectively and independently, are H, alkyl groups of 1 to 20 carbon atoms that may be substituted or aryl groups of 6 to 20 carbon atoms that may be substituted; k is an integer of 0 to 200; and a, b and c, respectively and independently, are integers of 0 to 20, excepting the case k=a=b=c=0.

5. The monomer of claim 3 wherein X in formula (1) or (2) is one substituent selected from substituents as represented by formulas (4) to (9) below:

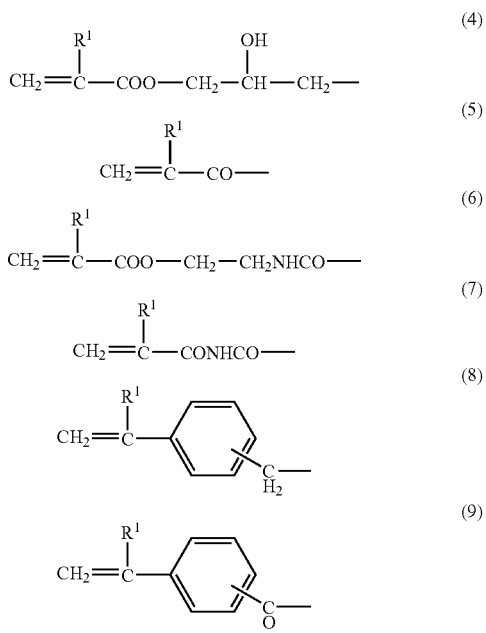

wherein, in formulas (4) to (9), $R^1$ is H or a methyl group.

6. The monomer of claim 3 wherein, said monomer is represented by formula (1), and X is a methacryloyl group or an acryloyl group, A is one substituent selected from tris(trimethylsiloxy)silyl groups, methylbis(trimethylsiloxy) silyl groups and dimethyl(trimethylsiloxy)silyl groups, m is an integer of 1 or 2 and n is an integer of 3.

7. A monomer represented by formula (2),

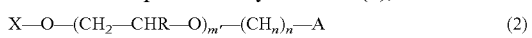

wherein X is a methacryloyl group or an acryloyl group, R is H, A is one substituent selected from tris(trimethylsiloxy)silyl groups, methylbis(trimethylsiloxy)silyl groups and dimethyl(trimethylsiloxy)silyl groups, m' is an integer of 2 or 3 and n is an integer of 3.

* * * * *